United States Patent
Khaid et al.

(10) Patent No.: US 9,999,613 B2
(45) Date of Patent: Jun. 19, 2018

(54) 2H-CHROMENE DERIVATIVES AS ANALGESIC AGENTS

(71) Applicant: OBSHESTVO S OGRANICHENNOI OTVETSVENNOSTJU "LEOFORS", Tomsk (RU)

(72) Inventors: Ekaterina Vladimirovna Khaid, Novosibirsk (RU); Alla Viktorovna Pavlova, Novosibirsk (RU); Oksana Stanislavovna Mikhal'Chenko, Novosibirsk (RU); Dina Vladimirovna Korchagina, Novosibirsk (RU); Tatiana Genrihovna Tolstikova, Novosibirsk (RU); Konstantin Petrovich Volcho, Novosibirsk (RU); Veniamin Abramovich Khazanov, Novosibirsk (RU); Nariman Faridovich Salakhutdinov, Novosibirsk (RU)

(73) Assignee: OBSHESTVO S OGRANICHENNOI OTVETSVENNOSTJU "LEOFORS", Tomsk (RU)

( * ) Notice: Subject to any disclaimer, the term of this patent is extended or adjusted under 35 U.S.C. 154(b) by 0 days. days.

(21) Appl. No.: 15/323,110

(22) PCT Filed: Jun. 10, 2015

(86) PCT No.: PCT/RU2015/000363
§ 371 (c)(1),
(2) Date: Dec. 30, 2016

(87) PCT Pub. No.: WO2016/007043
PCT Pub. Date: Jan. 14, 2016

(65) Prior Publication Data
US 2017/0157087 A1    Jun. 8, 2017

(30) Foreign Application Priority Data
Jul. 8, 2014    (RU) .................. 2014127953

(51) Int. Cl.
*A61K 31/381*    (2006.01)
(52) U.S. Cl.
CPC .................. *A61K 31/381* (2013.01)

(58) Field of Classification Search
CPC ........................ A61K 31/353; A61K 31/381
USPC ........................................................ 549/60
See application file for complete search history.

(56) References Cited

FOREIGN PATENT DOCUMENTS

| CN | 103705496 | * | 4/2014 |
|---|---|---|---|
| SU | 596169 | * | 2/1978 |
| WO | WO 2008130322 | * | 10/2008 |

OTHER PUBLICATIONS

Baishya; Synlett 2013, 24, 1137-1141.*
Pavlova; Med Chem Res 2015, 24, 3821-3830.*
Il'ina; Med Chem Res 2014, 23, 5063-5073.*
MikhalChenko; Med Chem Res 2013, 22, 3026-3034.*
Nazimova; Med Chem Res 2016, 25, 1369-1383.*
Sarmah; European Journal of Organic Chemistry 2014, 7561-7565.*
Sarmah; RSC Adv., 2014, 4, 22387-22397.*
Kurbakova; Med Chem Res 2014, 23, 1709-1717.*
Flessner; Journal of Molecular Catalysis A: Chemical 168 (2001) 247-256. (Year: 2001).*

* cited by examiner

Primary Examiner — Daniel R Carcanague
(74) Attorney, Agent, or Firm — John Alumit

(57) ABSTRACT

The invention relates to the use of the compound of general formula 1 or its spatial isomers

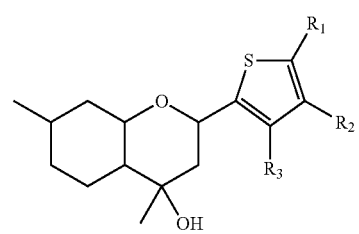

as an analgesic drug. The compounds have high activity, low toxicity, may be used in medicine.

2 Claims, No Drawings

2H-CHROMENE DERIVATIVES AS ANALGESIC AGENTS

FIELD OF THE INVENTION

The invention relates to the field of medicine, specifically, to drugs having analgesic effect.

BACKGROUND OF THE INVENTION

Analgesic drugs are known, that are nonnarcotic analgesics by their mechanism of action, such as acetylsalicylic acid, metamizole and others [1]. Data on activity in acetic acid induced writhing test ($ED_{50}$) and acute toxicity ($LD_{50}$) of the known drugs are presented in [2] and in Table 1.

TABLE 1

Toxicity and analgesic action of the known drugs [2].

| Drug | $ED_{50}$, mg/kg | $LD_{50}$, mg/kg |
| --- | --- | --- |
| Acetylsalicylic acid | 155 | 1600 |
| Metamizole | 55 | 3300 |
| Sodium diclofenac | 5 | 370 |

The disadvantage of acetylsalicylic acid is low activity and gastrointestinal toxicity; metamizole may induce hematopoiesis disorders, up to agranulocytosis.

Diclofenac sodium [3] was chosen as a prototype.

The disadvantages of sodium diclofenac are adverse gastrointestinal effects (gastrointestinal toxicity).

DESCRIPTION OF THE INVENTION

The goal of the invention is the development of new low toxic drugs possessing analgesic activity.

The goal is achieved by using the compounds of general formula 1

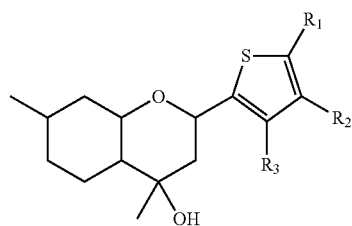

where $R_1$, $R_2$, $R_3$, may be identical or different; and may be a hydrogen atom, alkyl group, nitro group, halogen, as an analgesic drug, including their spatial isomers, including optically active isomers.

Compound 1a ($R_1$=$R_2$=$R_3$=H) was earlier synthesized by interaction of isopulegol 2 with thiophene-2-carbaldehyde in the presence of modified montmorillonite H-K10 clay under microwave radiation with 50% yield [4].

The derivatives of compound 1a, containing substituents in the heteroaromatic ring, weren't earlier described in the literature.

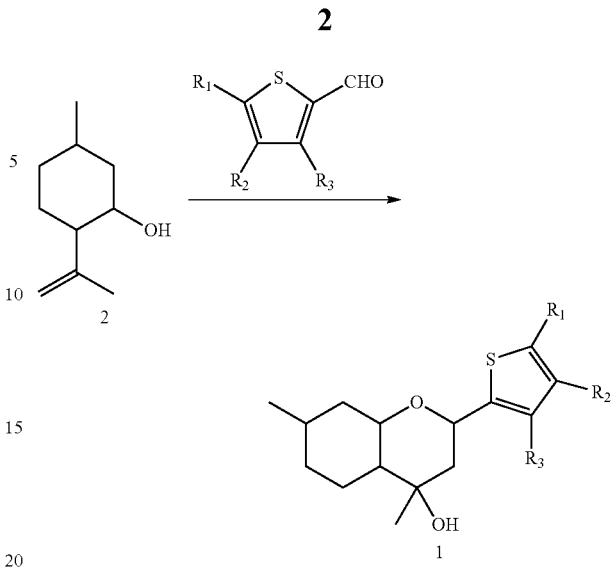

We have demonstrated that compound 1a may be produced with yield 78% by reaction of isopulegol 2 with thiophene-2-carbaldehyde in the presence of commercially available montmorillonite K10 clay without its prior chemical modification and in the absence of microwave radiation by simply keeping the reaction mixture without solvent during 1-2 hrs.

The derivatives of compound 1a, containing substituents in the heteroaromatic ring, can be synthesized by reaction of isopulegol 2 with substituted thiophene-2-carbaldehydes in the presence of K10 clay.

To produce compounds of general formula 1 as different stereoisomers, including optically active isomers, different spatial isomers of compound 2, including optically active isomers, may be used as raw materials.

Analgesic activity of compounds of general formula 1 was studied in the model of visceral pain «acetic acid induced writhing test» and thermal irritation test «hot plate» in white outbred mice of body mass 20-22 g in groups of 8 animals each after single administration in 1÷20 mg/kg doses.

Acetic acid induced writhing test was performed by intraperitoneal administration of 0.1 ml of 0.75% acetic acid to an animal. Activity was assessed by the quantity of writhing movements during 3 min.

Hot plate test characterizes thermal stimulus. The animals were placed on a copper plate, T=54° C. The effect was assessed by the duration of stay of the animal on the hot plate before the first vocalization.

It was determined, that compounds of general formula 1 in 10 mg/kg dose have potent analgesic activity in acetic acid induced writhing test, and compounds 1a ($R_1$=$R_2$=$R_3$=H) and 1d ($R_1$=H, $R_2$=Br, $R_3$=H) are more effective than sodium diclofenac, taken in the same dose (Table 2).

TABLE 2

Analgesic activity of compounds of general formula 1 in acetic acid induced writhing test in 10 mg/kg dose.

| Compound | | Writhes, quantity | | Pain reduction, %$^a$ |
| --- | --- | --- | --- | --- |
| | | Control | Agent | |
| 1a | $R_1 = R_2 = R_3 = H$ | 9.6 ± 0.9 | 4.3 ± 1.1 | 55** |
| 1b | $R_1 = R_2 = H, R_3 = Me$ | 10.9 ± 0.5 | 7.0 ± 0.6 | 36*** |

TABLE 2-continued

Analgesic activity of compounds of general formula 1 in acetic acid induced writhing test in 10 mg/kg dose.

| | | Writhes, quantity | | Pain reduction, |
|---|---|---|---|---|
| Compound | | Control | Agent | %[a] |
| 1c | $R_1$ = Me, $R_2$ = $R_3$ = H | 10.9 ± 0.5 | 6.6 ± 0.5 | 39*** |
| 1d | $R_1$ = H, $R_2$ = Br, $R_3$ = H | 9.6 ± 0.9 | 3.6 ± 1.5 | 63** |
| 1e | $R_1$ = Br, $R_2$ = $R_3$ = H | 9.6 ± 0.9 | 6.3 ± 1.2 | 34* |
| 1f | $R_1$ = $NO_2$, $R_2$ = $R_3$ = H | 11.1 ± 0.7 | 7.5 ± 1.2 | 32* |
| Sodium diclofenac | | 10.1 ± 1.9 | 5.0 ± 1.1 | 50*** |

[a]% pain reduction = $(t_{control} - t_{exp})/t_{control} \cdot 100\%$
*P < 0.05; P < 0.01; *P < 0.001 compared to control Data on analgesic activity in hot plate test is shown in Table 3. Reliable analgesic activity was observed for compound 1a ($R_1$=$R_2$=$R_3$=H).

TABLE 3

Analgesic compounds of general formula 1 in hot plate test in 10 mg/kg doses.

| | | Hot plate, sec. | | |
|---|---|---|---|---|
| Compound | | Control | Agent | Protection, %[a] |
| 1a | $R_1$ = $R_2$ = $R_3$ = H | 9.8 ± 0.8 | 13.1 ± 1.2 | 34* |
| 1b | $R_1$ = $R_2$ = H, $R_3$ = Me | 18.4 ± 2.1 | 12.8 ± 1.7 | — |
| 1c | $R_1$ = Me, $R_2$ = $R_3$ = H | 18.4 ± 2.1 | 17.4 ± 2.4 | — |
| 1d | $R_1$ = H, $R_2$ = Br, $R_3$ = H | 9.8 ± 0.8 | 13.6 ± 1.7 | 39 |
| 1e | $R_1$ = Br, $R_2$ = $R_3$ = H | 9.8 ± 0.8 | 11.6 ± 1.0 | 18 |
| 1f | $R_1$ = $NO_2$, $R_2$ = $R_3$ = H | 12.1 ± 1.3 | 14.5 ± 1.6 | 20 |
| Sodium diclofenac | | 9.6 ± 1.6 | 15.6 ± 2.4 | 62** |

[a]% protection = $(t_{exp} - t_{control})/t_{control} \cdot 100\%$
*P < 0.05; P < 0.01; * P < 0.001 compared to control Dose dependent effect of compound 1a, demonstrating high activity in both tests, was studied (Table 4). Data obtained show, that compound 1a has potent analgesic activity in both tests even in 1 mg/kg dose, being as effective as the reference drug sodium diclofenac in 10 mg/kg dose (Tables 2 and 3).

TABLE 4

Analgesic activity of compound 1a in acetic acid writhing test and hot plate test in different doses.

| Dose, mg/kg | Writhes, quantity | | Hot plate, sec. | |
|---|---|---|---|---|
| | Control | Agent (pain reduction, %)[a] | Control | Agent (protection, %)[b] |
| 20 | 11.0 ± 0.7 | 8.3 ± 0.5 (25)** | 10.7 ± 1.4 | 16.0 ± 2.6 (50) |
| 10 | 9.6 ± 0.9 | 4.3 ± 1.1 (55)** | 9.8 ± 0.8 | 13.1 ± 1.2 (34*) |
| 5 | 8.4 ± 0.6 | 4.9 ± 1.0 (42)** | 10.4 ± 1.2 | 16.3 ± 1.6 (57)* |
| 1 | 8.4 ± 0.6 | 2.4 ± 0.8 (71)*** | 10.4 ± 1.2 | 16.5 ± 1.9 (59)* |
| 0.5 | 10.1 ± 0.7 | 7.4 ± 1.3 (27) | 15.8 ± 1.6 | 20.3 ± 2.2 (28) |

[a]% pain reduction = $(t_{control} - t_{exp})/t_{control} \cdot 100\%$
[b]% protection = $(t_{exp} - t_{control})/t_{control} \cdot 100\%$
*P < 0.05; P < 0.01; *P < 0.001 compared to control Acute toxicity of compound 1a was studied in white outbred mice, body mass 20-22 g, after single intragastric administration using Kerber method. It was demonstrated, that compound 1a is a moderately toxic compound: $LD_{50}$ is over 1500 mg/kg, while therapeutic index ($IS_{50}$) is over 1500. Thus, compound 1a is considerably less toxic than sodium diclofenac ($LD_{50}$ 370 mg/kg [2]) and has much better therapeutic index ($IS_{50}$ of sodium diclofenac is 74 [2]).

Based on the aforementioned data, it can be concluded, that compounds of general formula 1 exhibit potent analgesic action in acetic acid induced writhing test. Compound 1a combines potent analgesic activity in acetic acid induced writhing test and hot plate test with low acute toxicity.

After detailed pharmacological studies, compounds of general formula 1 can used in pure form as well as a component of novel, low toxic, highly effective analgesic dosage forms.

The invention is illustrated by the following examples.

Example 1. Synthesis of 4,7-dimethyl-2-(thiophene-2-yl)octahydro-2H-chromene-4-ol 1a

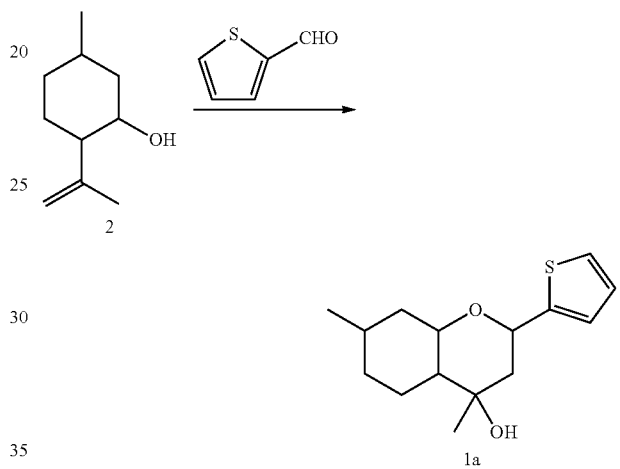

A solution of 0.29 g thiophene-2-carbaldehyde in 3 ml $CH_2Cl_2$ was added to a suspension of 1.3 g of K10 clay in 5 ml $CH_2Cl_2$, then a solution of 0.400 g isopulegol 2 in 3 ml $CH_2Cl_2$ was added. The solvent was evaporated and the reaction mixture was kept at room temperature during 60 min. Then 10 ml of EtOAc was added, the catalyst was filtered and the solvent was evaporated. The resulting mixture was separated at a column with 13 g silica gel (eluent: solution of 0 to 100% ethyl acetate in hexane). 0.543 g (yield 78%) of compound 1a was obtained. NMR $^1$H spectrum of compound 1a corresponds to the spectrum, published in the literature [4].

Example 2. Synthesis of 4,7-dimethyl-2-(3-methyl-thiophene-2-yl)octahydro-2H-chromene-4-ol 1b

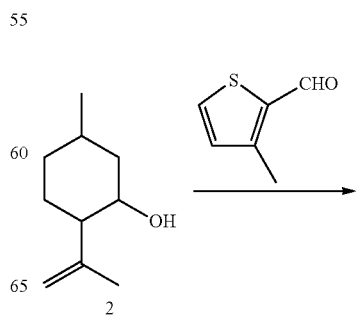

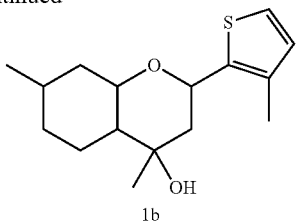
1b

Similar to Example 1, interaction of 0.300 g isopulegol 2 with 0.25 g 3-methylthiophene-2-carbaldehyde in the presence of 1.1 g K10 clay during 120 min resulted in 0.381 g (yield 70%) of compound 1b.

Spectrum NMR $^1$H (CDCl$_3$): 0.88-0.97 (m, 1H, H$_a$-8); 0.92 (d, J (16, 9a)=6.6 Hz, 3H, H-16); 1.03 (dddd, J (7a, 7e)=J (7a, 8a)=12.8 Hz, J (7a, 6a)=12.1 Hz, J (7a, 8e)=3.3 Hz, 1H, H$_a$-7); 1.11 (ddd, J (10a, 10e)=J (10a, 9a)=12.2 Hz, J (10a, 1a)=10.8 Hz, 1H, H$_a$-10); 1.28 (d, J (15, 4a)=0.7 Hz, 3H, H-15); 1.31 (ddd, J (6a, 7a)=12.1 Hz, J (6a, 1a)=10.2 Hz, J (6a, 7e)=3.3 Hz, 1H, H$_a$-6); 1.40-1.53 (m, 2H, H$_a$-9, OH); 1.72 (ddddd, J (8e, 8a)=12.9 Hz, J (8e, 7a)=J (8e, 9a)=J (8e, 7e)=3.3 Hz, J (8e, 10e)=2.0 Hz, 1H, H$_e$-8); 1.85 (ddq, J (4a, 4e)=12.7 Hz, J (4a, 3a)=11.7 Hz, J (4a, 15)=0.7 Hz, 1H, H$_a$-4); 1.91-1.97 (m, 1H, H$_e$-7); 1.95 (dd, J (4e, 4a)=12.7 Hz, J (4e, 3a)=2.4 Hz, 1H, H$_e$-4); 1.99 (dm, J (10e, 10a)=12.2 Hz, 1H, H$_e$-10); 2.19 (s, 3H, H-17); 3.26 (ddd, J (1a, 10a)=10.8 Hz, J (1a, 6a)=10.2 Hz, J (1a, 10e)=4.3 Hz, 1H, H$_a$-1); 4.71 (dd, J (3a, 4a)=11.7 Hz, J (3a, 4e)=2.4 Hz, 1H, H$_a$-3); 6.75 (d, J (13, 12)=5.0 Hz, 1H, H-13); 7.09 (d, J (12, 13)=5.0 Hz, 1H, H-12). Spectrum NMR $^{13}$C (CDCl$_3$): 77.63 (d, C-1); 71.09 (d, C-3); 49.70 (t, C-4); 70.64 (s, C-5); 51.91 (d, C-6); 22.94 (t, C-7); 34.26 (d, C-9); 41.32 (t, C-10); 138.34 (s, C-11); 122.92 (d, C-12); 129.72 (d, C-13); 133.29 (s, C-14); 21.09 (q, C-15); 22.03 (q, C-16); 13.63 (q, C-17). HR-MS: 280.1488 (M$^+$, C$_{16}$H$_{24}$O$_2$S$^+$; calc. 280.1492).

Example 3. Synthesis of 4,7-dimethyl-2-(5-methyl-thiophene-2-yl)octahydro-2H-chromene-4-ol 1c

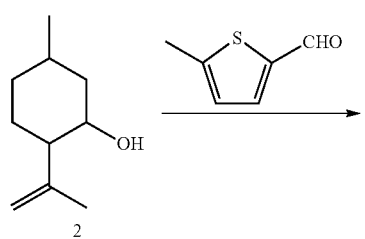

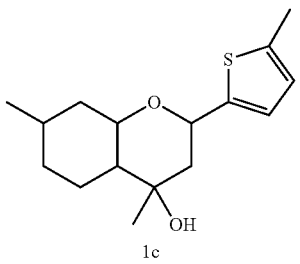
1c

Similar to Example 1, interaction of 0.300 g isopulegol 2 with 0.25 g 5-methylthiophene-2-carbaldehyde in the presence of 1.1 g K10 clay during 120 min resulted in 0.386 g (yield 71%) of compound 1c.

Spectrum NMR $^1$H (CDCl$_3$): 0.87-0.96 (m, 1H, H$_a$-8); 0.92 (d, J (16, 9a)=6.6 Hz, 3H, H-16); 1.02 (dddd, J (7a, 7e)=J (7a, 8a)=12.8 Hz, J (7a, 6a)=12.2 Hz, J (7a, 8e)=3.3 Hz, 1H, H$_a$-7); 1.09 (ddd, J (10a, 10e)=J (10a, 9a)=12.3 Hz, J (10a, 1a)=10.8 Hz, 1H, H$_a$-10); 1.25 (d, J (15, 4a)=0.8 Hz, 3H, H-15); 1.28 (ddd, J (6a, 7a)=12.2 Hz, J (6a, 1a)=10.2 Hz, J (6a, 7e)=3.3 Hz, 1H, H$_a$-6); 1.39-1.52 (m, 2H, H$_a$-9, OH); 1.72 (ddddd, J (8e, 8a)=12.8 Hz, J (8e, 7a)=J (8e, 9a)=J (8e, 7e)=3.3 Hz, J (8e, 10e)=2.0 Hz, 1H, H$_e$-8); 1.86 (ddq, J (4a, 4e)=12.7 Hz, J (4a, 3a)=11.7 Hz, J (4a, 15)=0.8 Hz, 1H, H$_a$-4); 1.93 (dddd, J (7e, 7a)=12.8 Hz, J (7e, 6a)=J (7e, 8a)=J (7e, 8e)=3.3 Hz, 1H, H$_e$-7); 1.99 (dm, J (10e, 10a)=12.3 Hz, 1H, H$_e$-10); 2.01 (dd, J (4e, 4a)=12.7 Hz, J (4e, 3a)=2.2 Hz, 1H, H$_e$-4); 2.42 (d, J (17, 13)=1.1 Hz, 3H, H-17); 3.24 (ddd, J (1a, 10a)=10.8 Hz, J (1a, 6a)=10.2 Hz, J (1a, 10e)=4.3 Hz, 1H, H$_a$-1); 4.59 (dd, J (3a, 4a)=11.7 Hz, J (3a, 4e)=2.2 Hz, 1H, H$_a$-3); 6.56 (dq, J (13, 14)=3.4 Hz, J (13, 17)=1.1 Hz, 1H, H-13); 6.73 (d, J (14, 13)=3.4 Hz, 1H, H-14). Spectrum NMR $^{13}$C (CDCl$_3$): 77.43 (d, C-1); 72.54 (d, C-3); 49.58 (t, C-4); 70.69 (s, C-5); 51.89 (d, C-6); 22.93 (t, C-7); 34.26 (t, C-8); 31.38 (d, C-9); 41.35 (t, C-10); 142.89 (s, C-11); 139.12 (s, C-12); 124.26 (d, C-13); 123.50 (d, C-14); 21.17 (q, C-15); 22.04 (q, C-16); 15.16 (q, C-17). HR-MS: 280.1491 (M$^+$, C$_{16}$H$_{24}$O$_2$S$^+$; calc. 280.1492).

Example 4. Synthesis of 4,7-dimethyl-2-(4-bromo-thiophene-2-yl)octahydro-2H-chromene-4-ol 1d

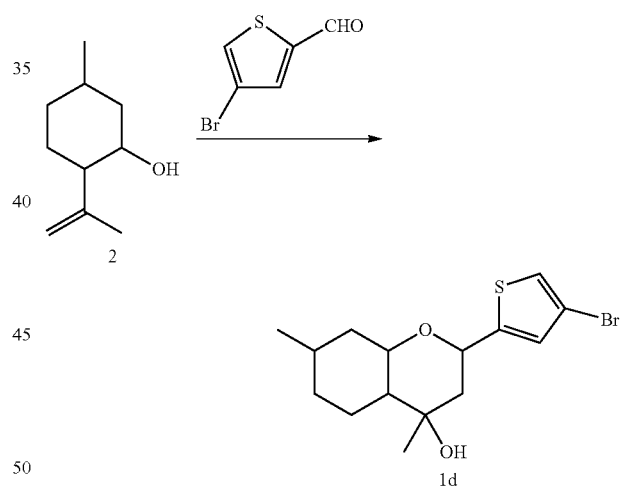
1d

Similar to Example 1, interaction of 0.300 g isopulegol 2 with 0.37 g 4-bromothiophene-2-carbaldehyde in the presence of 1.4 g K10 clay during 120 min resulted in 0.499 g (yield 74%) of compound 1d.

Spectrum NMR $^1$H (CDCl$_3$): 0.87-0.96 (m, 1H, H$_a$-8); 0.93 (d, J (16, 9a)=6.6 Hz, 3H, H-16); 1.02 (dddd, J (7a, 7e)=J (7a, 8a)=12.8 Hz, J (7a, 6a)=12.1 Hz, J (7a, 8e)=3.2 Hz, 1H, H$_a$-7); 1.10 (ddd, J (10a, 10e)=J (10a, 9a)=12.2 Hz, J (10a, 1a)=11.1 Hz, 1H, H$_a$-10); 1.26 (d, J (15, 4a)=0.7 Hz, 3H, H-15); 1.29 (ddd, J (6a, 7a)=12.1 Hz, J (6a, 1a)=10.1 Hz, J (6a, 7e)=3.2 Hz, 1H, H$_a$-6); 1.39-1.50 (m, 1H, H$_a$-9); 1.56 (br.s, OH); 1.72 (dm, J (8e, 8a)=12.8 Hz, others J<3.5 Hz, 1H, H$_e$-8); 1.82 (ddq, J (4a, 4e)=12.7 Hz, J (4a, 3a)=11.7 Hz, J (4a, 15)=0.7 Hz, 1H, H$_a$-4); 1.93 (dddd, J (7e, 7a)=12.8 Hz, J (7e, 6a)=J (7e, 8a)=J (7e, 8e)=3.2 Hz, 1H, H$_e$-7); 1.99

(dddd, J (10e, 10a)=12.8 Hz, J (10e, 1a)=4.3 Hz, J (10e, 9a)=3.7 Hz, J (10e, 8e)=2.0 Hz, 1H, H$_e$-10); 2.01 (dd, J (4e, 4a)=12.7 Hz, J (4e, 3a)=2.2 Hz, 1H, H$_e$-4); 3.26 (ddd, J (1a, 10a)=11.1 Hz, J (1a, 6a)=10.1 Hz, J (1a, 10e)=4.3 Hz, 1H, H$_a$-1); 4.62 (ddd, J (3a, 4a)=11.7 Hz, J (3a, 4e)=2.2 Hz, J (3a, 14)=0.8 Hz, 1H, H$_a$-3); 6.86 (dd, J (14, 12)=1.5 Hz, J (14, 3a)=0.8 Hz, 1H, H-14); 7.11 (d, J (12, 14)=1.5 Hz, 1H, H-12). Spectrum NMR $^{13}$C (CDCl$_3$): 77.65 (d, C-1); 72.07 (d, C-3); 49.54 (t, C-4); 70.52 (s, C-5); 51.82 (d, C-6); 22.89 (t, C-7); 34.20 (t, C-8); 31.36 (d, C-9); 41.22 (t, C-10); 146.74 (s, C-11); 121.72 (d, C-12); 108.88 (s, C-13); 126.11 (d, C-14); 21.16 (q, C-15); 22.02 (q, C-16). HR-MS: 345.0445 (M$^+$, C$_{15}$H$_{21}$O$_2$SBr$^+$; calc. 345.0440).

Example 5. Synthesis of 4,7-dimethyl-2-(5-bromo-thiophene-2-yl)octahydro-2H-chromene-4-ol 1e

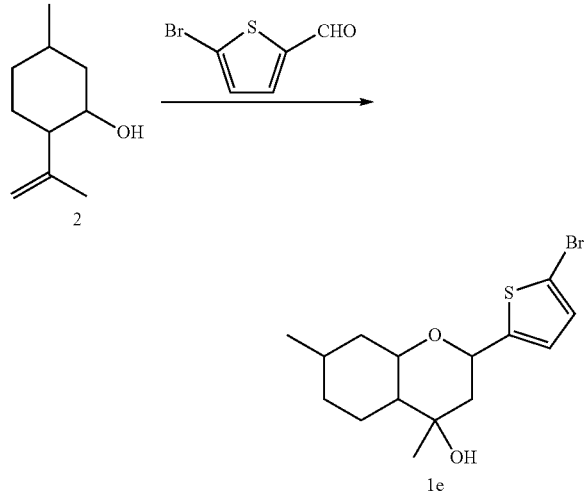

Similar to Example 1, interaction of 0.300 g isopulegol 2 with 0.37 g 5-bromothiophene-2-carbaldehyde in the presence of 1.4 g K10 clay during 120 min resulted in 0.512 g (yield 76%) of compound 1e.

Spectrum NMR $^1$H (CDCl$_3$): 0.87-0.96 (m, 1H, H$_a$-8); 0.92 (d, J (16, 9a)=6.6 Hz, 3H, H-16); 1.02 (dddd, J (7a, 7e)=J (7a, 8a)=12.8 Hz, J (7a, 6a)=12.2 Hz, J (7a, 8e)=3.3 Hz, 1H, H$_a$-7); 1.09 (ddd, J (10a, 10e)=J (10a, 9a)=12.2 Hz, J (10a, 1a)=10.8 Hz, 1H, H$_a$-10); 1.25 (d, J (15, 4a)=0.8 Hz, 3H, H-15); 1.28 (ddd, J (6a, 7a)=12.2 Hz, J (6a, 1a)=10.2 Hz, J (6a, 7e)=3.3 Hz, 1H, H$_a$-6); 1.37-1.50 (m, 2H, H$_a$-9, OH); 1.72 (dm, J (8e, 8a)=12.8 Hz, others J<3.5 Hz, 1H, H$_e$-8); 1.81 (ddq, J (4a, 4e)=12.7 Hz, J (4a, 3a)=11.8 Hz, J (4a, 15)=0.8 Hz, 1H, H$_a$-4); 1.92 (dddd, J (7e, 7a)=12.8 Hz, J (7e, 6a)=J (7e, 8a)=J (7e, 8e)=3.3 Hz, 1H, H$_e$-7); 1.98 (dddd, J (10e, 10a)=12.2 Hz, J (10e, 1a)=4.3 Hz, J (10e, 9a)=3.7 Hz, J (10e, 8e)=2.0 Hz, 1H, H$_e$-10); 2.01 (dd, J (4e, 4a)=12.7 Hz, J (4e, 3a)=2.2 Hz, 1H, H$_e$-4); 3.24 (ddd, J (1a, 10a)=10.8 Hz, J (1a, 6a)=10.2 Hz, J (1a, 10e)=4.3 Hz, 1H, H$_a$-1); 4.59 (ddd, J (3a, 4a)=11.8 Hz, J (3a, 4e)=2.2 Hz, J (3a, 14)=0.8 Hz, 1H, H$_a$-3); 6.68 (dd, J (14, 13)=3.8 Hz, 1H, H-14); 6.86 (d, J (13, 14)=3.8 Hz, 1H, H-13). Spectrum NMR $^{13}$C (CDCl$_3$): 77.58 (d, C-1); 72.53 (d, C-3); 49.42 (t, C-4); 70.54 (s, C-5); 51.84 (d, C-6); 22.89 (t, C-7); 34.20 (t, C-8); 31.35 (d, C-9); 41.23 (t, C-10); 147.17 (s, C-11); 111.45 (s, C-12); 129.01 (d, C-13); 123.55 (d, C-14); 21.16 (q, C-15); 22.02 (q, C-16); HR-MS: 345.0442 (M$^+$, C$_{15}$H$_{21}$O$_2$SBr$^+$; calc. 345.0440).

Example 6. Synthesis 4,7-dimethyl-2-(5-nitrothiophene-2-yl)octahydro-2H-chromene-4-ol 1f

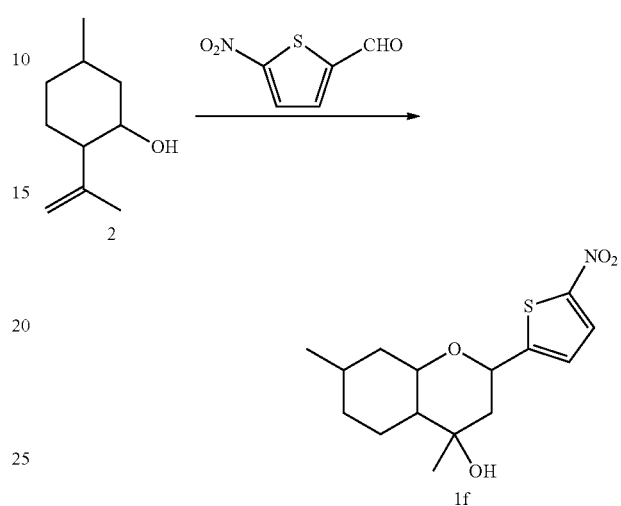

Similar to Example 1, interaction of 0.400 g isopulegol 2 with 0.407 g 5-nitrothiophene-2-carbaldehyde in the presence of 1.6 g K10 clay during 60 min resulted in 0.400 g (yield 50%) of compound 1f.

Spectrum NMR $^1$H (CDCl$_3$): 0.86-0.95 (m, 1H, H$_a$-8); 0.93 (d, J (16, 9a)=6.6 Hz, 3H, H-16); 1.01 (dddd, J (7a, 7e)=J (7a, 8a)=12.8 Hz, J (7a, 6a)=12.1 Hz, J (7a, 8e)=3.4 Hz, 1H, H$_a$-7); 1.09 (ddd, J (10a, 10e)=J (10a, 9a)=12.2 Hz, J (10a, 1a)=10.9 Hz, 1H, H$_a$-10); 1.26 (d, J (15, 4a)=0.7 Hz, 3H, H-15); 1.29 (ddd, J (6a, 7a)=12.1 Hz, J (6a, 1a)=10.2 Hz, J (6a, 7e)=3.2 Hz, 1H, H$_a$-6); 1.39-1.50 (m, 1H, H$_a$-9); 1.72 (dm, J (8e, 8a)=12.8 Hz, others J<3.5 Hz, 1H, H$_e$-8); 1.75 (ddq, J (4a, 4e)=12.8 Hz, J (4a, 3a)=11.9 Hz, J (4a, 15)=0.7 Hz, 1H, H$_a$-4); 1.92 (dddd, J (7e, 7a)=12.8 Hz, J (7e, 6a)=J (7e, 8a)=J (7e, 8e)=3.2 Hz, 1H, H$_e$-7); 1.99 (dddd, J (10e, 10a)=12.2 Hz, J (10e, 1a)=4.3 Hz, J (10e, 9a)=3.7 Hz, J (10e, 8e)=1.9 Hz, 1H, H$_e$-10); 2.04 (dd, J (4e, 4a)=12.8 Hz, J (4e, 3a)=2.2 Hz, 1H, H$_e$-4); 3.27 (ddd, J (1a, 10a)=10.9 Hz, J (1a, 6a)=10.2 Hz, J (1a, 10e)=4.3 Hz, 1H, H$_a$-1); 4.65 (ddd, J (3a, 4a)=11.9 Hz, J (3a, 4e)=2.2 Hz, J (3a, 14)=0.9 Hz, 1H, H$_a$-3); 6.82 (dd, J (14, 13)=4.2 Hz, J (14, 3a)=0.9 Hz, 1H, H-14); 7.75 (d, J (13, 14)=4.2 Hz, 1H, H-13). Spectrum NMR $^{13}$C (CDCl$_3$): 77.81 (d, C-1); 72.38 (d, C-3); 49.42 (t, C-4); 70.25 (s, C-5); 51.68 (d, C-6); 22.78 (t, C-7); 34.09 (t, C-8); 31.25 (d, C-9); 41.04 (t, C-10); 154.79 (s, C-11); 150.56 (s, C-12); 128.17 (d, C-13); 121.75 (d, C-14); 21.01 (q, C-15); 21.95 (q, C-16 HR-MS: 311.1185 (M$^+$, (C$_{15}$H$_{21}$O$_4$NS)$^+$; calc. 311.1186).

Example 7. Study of Analgesic Activity of Compounds of General Formula 1 in Acetic Acid Induced Writhing Test Tests were carried out in outbred male mice with body mass 22-25 g. Experimental groups were formed, with 8 animals in each. <<Acetic writhes>> were produced by intraperitoneal administration of 0.75% acetic acid, 0.1 ml per animal. Test compounds were administered once intragastrically an hour before acetic acid administration. Animals that received only acetic acid were used as control. Activity was assessed by the quantity of writhes during 3 min.

The results are shown in Tables 2 and 4.

Compounds of general formula 1 were demonstrated to have potent analgesic activity in acetic acid induced writhing test.

Example 8. Studying the Analgesic Activity of Compounds of General Formula 1 in Hot Plate Test Tests were carried out in outbred male mice of body mass 22-25 g. Experimental groups were formed, with 8 animals in each. The animals were placed on a copper hot plate, T=54° C. The effects were assessed by the duration of animal stay on the hot plate before the first <<vocalisation>>, in seconds.

Test compounds were administered once intragastrically an hour before the test. Control animals received the corresponding solvent. The results are shown in Tables 3 and 4. Compound of general formula 1a was demonstrated to have potent analgesic activity in hot plate test.

REFERENCES

1. Mashkovsky M. D. Drugs. V. 1. M.: Medicine. 2007.
2. Shubaev R. D., Mashkovsky M. D., Schwartz G. Y., Pokryshkin V. I. Comparative pharmacological activity of modern nonsteroidal anti-inflammatory drugs. Chem. Pharm. Journal. 1986. V. 20. No 1. P. 33-39.
3. Vidal Reference book. Drugs in Russia: Reference book. M.: Astra Pharm Service. 2002. 3-90.
4. Baishya G., Sarmah B., Hazarika N. Synlett 2013, Vol. 24, P. 1137-1141.

The invention claimed is:

1. A method of reducing pain in a subject, comprising administration of a compound of formula 1, or a stereoisomer thereof, to the subject

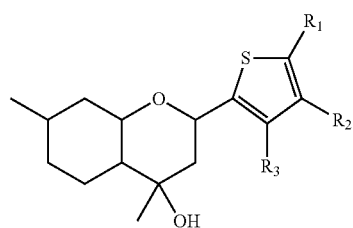

wherein $R_1$, $R_2$, and $R_3$ are identical or different, and are selected from the group consisting of a hydrogen atom, an alkyl group, a nitro group, and a halogen.

2. The method of claim 1, wherein one or more of $R_1$, $R_2$, and $R_3$ is an alkyl group, a nitro group, or a halogen.

* * * * *